United States Patent
Michlig Gonzalez et al.

(10) Patent No.: US 10,188,678 B2
(45) Date of Patent: Jan. 29, 2019

(54) COMPOSITION COMPRISING CINNAMALDEHYDE AND ZINC TO IMPROVE SWALLOWING

(71) Applicant: NESTEC S.A., Vevey (CH)

(72) Inventors: Stephanie Michlig Gonzalez, Le Mont-sur-Lausanne (CH); Jenny Meylan Merlini, Lausanne (CH); Adam Burbidge, Arzier (CH); Johannes Le Coutre, Pully (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 15/127,477

(22) PCT Filed: Mar. 17, 2015

(86) PCT No.: PCT/EP2015/055479
§ 371 (c)(1),
(2) Date: Sep. 20, 2016

(87) PCT Pub. No.: WO2015/140124
PCT Pub. Date: Sep. 24, 2015

(65) Prior Publication Data
US 2017/0224729 A1    Aug. 10, 2017

Related U.S. Application Data

(60) Provisional application No. 61/968,105, filed on Mar. 20, 2014.

(51) Int. Cl.
| | | |
|---|---|---|
| A61K 9/00 | (2006.01) | |
| A23L 29/00 | (2016.01) | |
| A23L 33/10 | (2016.01) | |
| A23L 33/16 | (2016.01) | |
| A61K 31/11 | (2006.01) | |
| A61K 33/30 | (2006.01) | |
| A23L 33/115 | (2016.01) | |

(52) U.S. Cl.
CPC .............. *A61K 33/30* (2013.01); *A23L 29/03* (2016.08); *A23L 33/10* (2016.08); *A23L 33/115* (2016.08); *A23L 33/16* (2016.08); *A61K 9/0056* (2013.01); *A61K 31/11* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 4,727,197 A | * | 2/1988 | Pittet | A23G 4/06 568/433 |
| 2003/0224090 A1 | * | 12/2003 | Pearce | A23G 3/36 426/89 |
| 2004/0258823 A1 | * | 12/2004 | Dufresne | A21D 2/00 426/573 |

FOREIGN PATENT DOCUMENTS

| | | |
|---|---|---|
| WO | 0128503 | 4/2001 |
| WO | 2005089206 | 9/2005 |
| WO | 2015011037 | 1/2015 |

OTHER PUBLICATIONS

Cinnamon spice nutrition facts. Nutrition and you, available online from Nov. 11, 2010 [retrieved on Sep. 28, 2017]. Retrieved from the internet: <http://www.nutrition-and-you.com/cinnamon-spice.html>.*
Cinnamon spice nutrition facts. Nutrition and you, available online from Nov. 11, 2010 [retrieved on Sep. 28, 2017]. Retrieved from the internet.*
Sura et al. Clinical Interventions in Aging vol. 7, pp. 287-298; publication year: 2012.*
Hughes et al. British J Pharmacol. vol. 162, pp. 1239-1249; publication year: 2011.*
Ebihara et al. British Journal of Clinical Pharmacology vol. 62, No. 3, pp. 369-371; publication year: 2006.*
Cinnamaldehyde website [online]. retrieved on Sep. 28, 2017. Retrieved from the Internet: <http://www.chm.bris.ac.uk.motm/cinnamaldehyde/cinnh.htm>.*
Ebihara et al. "Effects of menthol on the triggering of the swallowing reflex in elderly patients with dysphagia" British Journal of Clinical Pharmacology, 2006, vol. 62, No. 3, pp. 369-371.
Ebihara, Satoru "New therapeutic strategy of aspiration pneumonia using sensory stimuli" Journal of Pharmacological Studies, 2010, vol. 112, No. Suppl. 1, p. 39P, XP009183785.
Rofes et al. "Neuogenic and oropharyngeal dysphagia" Annals of the New York Academy of Sciences, 2013, vol. 1300, pp. 1-10.

* cited by examiner

Primary Examiner — Katherine Peebles
(74) Attorney, Agent, or Firm — K&L Gates LLP

(57) ABSTRACT

Compositions comprise an amount of cinnamaldehyde that is orally tolerable, thus avoiding an unpleasant mouth feeling, and also tolerable in the gastrointestinal tract. The amount of cinnamaldehyde is supplemented by zinc, and the combination is effective to promote a swallowing reflex. The composition comprising the combination of cinnamaldehyde and zinc can be used in a method to treat dysphagia and/or prevent aspiration pneumonia from dysphagia. In an embodiment, the composition comprising cinnamaldehyde is administered to a human. The composition comprising cinnamaldehyde may be a medicament, a food product or a supplement to a food product.

8 Claims, 1 Drawing Sheet

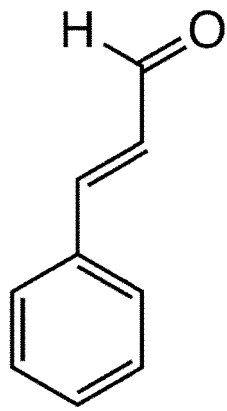
Fig. 1. The chemical structure of cinnamaldehyde.
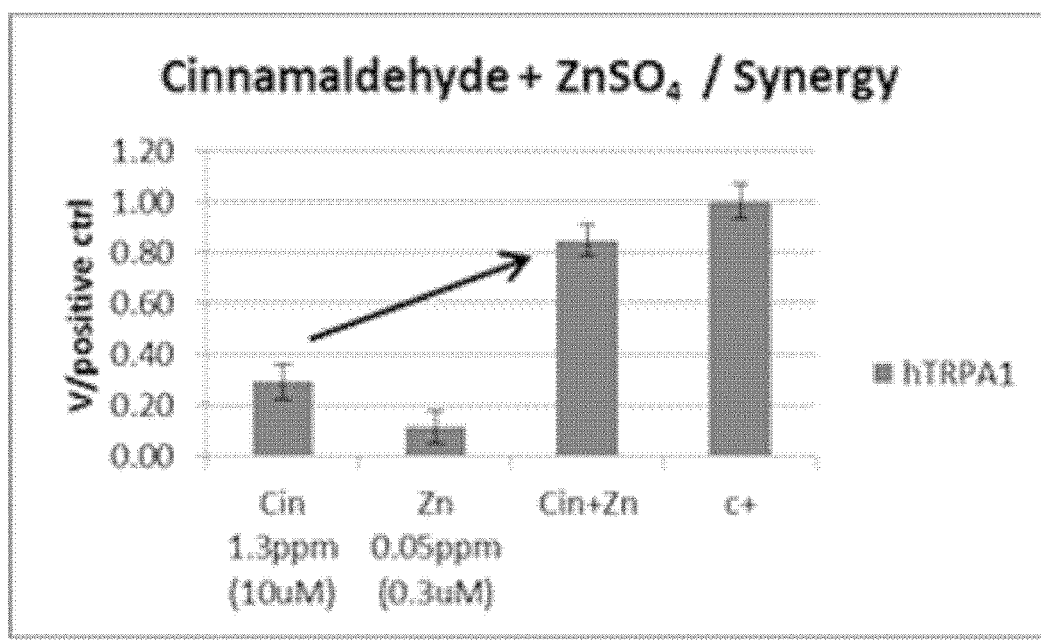
Fig. 2. *In vitro* evaluation of cinnamaldehyde and zinc synergy.

COMPOSITION COMPRISING CINNAMALDEHYDE AND ZINC TO IMPROVE SWALLOWING

CROSS REFERENCE TO RELATED APPLICATIONS

The present application is a National Stage of International Application No. PCT/EP2015/055479, filed on Mar. 17, 2015, which claims priority to U.S. Provisional Patent Application No. 61/968,105, filed Mar. 20, 2014, the entire contents of which are being incorporated herein by reference.

BACKGROUND

The present disclosure generally relates to methods and compositions for improving the swallowing reflex. More specifically, the present disclosure relates to improving the swallowing reflex by administering an amount of cinnamaldehyde and zinc that provides a minimal flavor impact.

Dysphagia is a condition typified by a decreased ability to swallow. The normal swallow involves three distinct phases which are interdependent and well coordinated, namely the oral, pharyngeal and esophageal phases. In the oral phase, which is under voluntary control, food that has been chewed and mixed with saliva is formed into a bolus for delivery by voluntary tongue movements to the back of the mouth, into the pharynx. The pharyngeal phase is involuntary and is triggered by the bolus passing through the faucial pillars into the pharynx. The three constrictors of the pharynx contract to propel the bolus toward the upper oesophageal sphincter. Simultaneously, the soft palate closes the nasopharynx. The larynx moves upward to prevent food or liquid from entering the airway, which is aided by the backward tilt of the epiglottis and closure of the vocal folds. The oesophageal phase is also involuntary and starts with the relaxation of the upper oesophageal sphincter followed by peristalsis, which pushes the bolus down to the stomach.

Esophageal dysphagia affects a large number of individuals of all ages, but is generally treatable with medications and is considered a less serious form of dysphagia. On the other hand, oral pharyngeal dysphagia is a very serious condition and is generally not treatable with medication. Oral pharyngeal dysphagia also affects individuals of all ages but is more prevalent in older individuals. Worldwide, oral pharyngeal dysphagia affects approximately 22 million people over the age of 50 years.

The consequences of untreated or poorly managed oral pharyngeal dysphagia can be severe, including dehydration, malnutrition, airway obstruction with solid foods (choking), and airway aspiration of liquids and semi-solid foods which promotes aspiration pneumonia and/or pneumonitis. Severe oral pharyngeal dysphagia may require nutrition to be supplied by tube feeding. Mild to moderate oral pharyngeal dysphagia requires the texture of foods to be modified in order to minimize the likelihood of choking or aspiration.

Oral pharyngeal dysphagia is often a consequence of an acute event, such as a stroke, brain injury, or surgery for oral or throat cancer. In addition, radiotherapy and chemotherapy may weaken the muscles and degrade the nerves associated with the physiology and nervous innervation of the swallow reflex. Individuals with progressive neuromuscular diseases, such as Parkinson's disease, also commonly experience increasing difficulty in swallow initiation.

Improving an individual's ability and efficiency to swallow improves the individual's safety through reduced risk of pulmonary aspiration. An efficient swallow may permit greater independence from feeding assistance and/or reduced length of time spent in feeding-assistance during meal consumption. An efficient swallow also reduces the viscosity of liquids required for safety (e.g., pudding, honey and nectar thickness products) and may also limit the use of texture-modified foods. All of these previously described factors are aimed at improving an individual's quality of life.

Research on the molecular mechanisms underlying pungent sensations revealed the existence of two cation channels, TRPV1 (transient receptor potential V1) and TRPA1 (transient receptor potential A1) that are expressed in the somatosensory fibers innervating the oral cavity. TRPV1 is the receptor for heat and burning sensations such as capsaicin, the spicy compound of chili peppers. TRPA1 responds to cold and pungent compounds; at moderate concentrations, TRPA1 agonists exhibit a pleasant tingling sensation.

Oral administration of the TRPV1 agonist capsaicin has been shown to promote a swallow reflex, but capsaicin is a particularly pungent and toxic compound. Physiological effects associated with oral administration of capsaicin include a burning sensation of heat from the mid-tongue to the throat, shortness of breath, fainting, nausea, and spontaneous vomiting. As a result, only small quantities of capsaicin may be administered without causing discomfort to the individual. Food products containing capsaicin are frequently not accepted by the consumer because such products provide a very unpleasant mouth feeling. In particular, the burning effects are considered to be very unsavory, affecting the consumption of the food product.

The cinnamon-derived compound cinnamaldehyde is a $\alpha,\beta$-unsaturated aldehyde that activates TRPA1, but not TRPV1 or TRPM8, with an EC50 of approximately 10 µM. Cinnamaldehyde interacts with TRPA1 in a covalent manner. Cinnamaldehyde has a flavor that is less intense than capsaicin. Nevertheless, cinnamaldehyde is pungent at relatively high concentrations and has a strong cinnamon flavor.

SUMMARY

The present inventors surprisingly and unexpectedly identified a synergy of cinnamaldehyde and zinc on the pharmacological activity of TRPA1. Using this synergy, the effective amount of cinnamaldehyde can be decreased by supplementing the cinnamaldehyde with small amount of zinc. The decreased amount of cinnamaldehyde can reduce the aromatic impact while maintaining a good efficacy on the activity of TRPA1. Moreover, the synergy only requires a low concentration of zinc (in vitro <1 µM), which is advantageous because dysphagic patients may already receive zinc through their diet, especially if supplements are consumed.

The present inventors identified a synergy of cinnamaldehyde and zinc on the pharmacological activity of TRPA1 expressed in a cellular model. To the best knowledge of the inventors, this is the first time that the synergy of this combination has been shown.

Accordingly, in a general embodiment, the present disclosure provides a method for promoting a swallowing reflex comprising administering to a patient in need thereof a composition comprising cinnamaldehyde and zinc.

In an embodiment, the cinnamaldehyde is present in the composition in an amount that is tolerable to ingest and, in combination with the zinc, effective to promote a swallowing reflex in the patient.

In an embodiment, promotion of the swallowing reflex comprises an effect selected from the group consisting of provoking the swallowing reflex, increasing the ability of the patient to swallow, increasing the efficacy of the swallowing reflex, decreasing a delay in swallowing, and combinations thereof.

In an embodiment, the composition comprises cinnamon essential oil extract that provides at least a portion of the cinnamaldehyde.

In an embodiment, at least a portion of the cinnamaldehyde is selected from the group consisting of isolated cinnamaldehyde and synthesized cinnamaldehyde.

In an embodiment, at least a portion of the zinc is selected from the group consisting of zinc chloride, zinc sulfate, zinc lactate, zinc citrate and combinations thereof.

In another embodiment, the present disclosure provides a method for treating dysphagia. The method comprises administering to a patient having dysphagia a composition comprising cinnamaldehyde and zinc.

In an embodiment, the dysphagia is oral pharyngeal dysphagia associated with a condition selected from the group consisting of cancer, cancer chemotherapy, cancer radiotherapy, surgery for oral cancer, surgery for throat cancer, a stroke, a brain injury, a progressive neuromuscular disease, neurodegenerative diseases, an elderly age of the patient, and combinations thereof.

In another embodiment, the present disclosure provides a method for preventing aspiration pneumonia from dysphagia comprising administering to a patient at risk thereof a composition comprising cinnamaldehyde and zinc.

In an embodiment, the cinnamaldehyde is present in the composition in an amount that is tolerable to ingest and, in combination with the zinc, effective to promote a swallowing reflex in the patient.

In another embodiment, the present disclosure provides a composition comprising cinnamaldehyde and zinc.

In an embodiment, the cinnamaldehyde is present in the composition in an amount that is orally tolerable and, in combination with the zinc in the composition, effective to promote a swallowing reflex.

In an embodiment, the composition is a food product in which the cinnamaldehyde is present at a concentration of about 100 ppm or less.

In an embodiment, the composition is a food product in which the cinnamaldehyde:zinc ratio is 1:0.5 to 1:0.005, preferably 1:0.03 (in molarity).

In an embodiment, the composition is a food product comprising a component selected from the group consisting of protein, carbohydrate, fat and combinations thereof.

An advantage of the present disclosure is to promote a swallowing reflex.

Another advantage of the present disclosure is to treat dysphagia.

Still another advantage of the present disclosure is to prevent aspiration pneumonia from dysphagia.

Yet another advantage of the present disclosure is to promote a swallowing reflex with ingredients that can be easily and safely used in food products.

An additional advantage of the present disclosure is to promote a swallowing reflex with a naturally-occurring compound that can be found in spices.

Another advantage of the present disclosure is to promote a swallowing reflex with tolerable side effects or no side effects.

Yet another advantage of the present disclosure is to promote a swallowing reflex with a compound that has increased acceptability, reduced pungency, and improved tolerance in the gastrointestinal tract relative to capsaicin.

An advantage of the present disclosure is to treat patients having a swallowing impairment.

Another advantage of the present disclosure is to supplement cinnamaldehyde with zinc so that less cinnamaldehyde is required to promote a swallowing reflex.

Additional features and advantages are described herein, and will be apparent from, the following Detailed Description and the Figures.

BRIEF DESCRIPTION OF THE FIGURES

FIG. 1 shows the chemical structure of cinnamaldehyde.

FIG. 2 shows a graph of in vitro measurement of the activity of TRP channels expressed in CHO cells by measuring the intracellular calcium concentration with a fluorescent dye.

DETAILED DESCRIPTION

All percentages expressed herein are by weight of the total weight of the composition unless expressed otherwise. When reference is made to the pH, values correspond to pH measured at 25° C. with standard equipment. As used in this disclosure and the appended claims, the singular forms "a," "an" and "the" include plural referents unless the context clearly dictates otherwise. As used herein, "about" is understood to refer to numbers in a range of numerals, for example the range of −10% to +10% of the referenced number. Moreover, all numerical ranges herein should be understood to include all integers, whole or fractions, within the range. The compositions disclosed herein may lack any element that is not specifically disclosed herein. Thus, a disclosure of an embodiment using the term "comprising" includes a disclosure of embodiments "consisting essentially of" and "consisting of" the components identified.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

As used herein, an "effective amount" is an amount that prevents a deficiency, treats a disease or medical condition in an individual or, more generally, reduces symptoms, manages progression of the diseases or provides a nutritional, physiological, or medical benefit to the individual.

"Animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human that can benefit from the treatment.

An animal is considered "elderly" if it has surpassed the first two thirds of the average expected lifespan in its country of origin, preferably if it has surpassed the first three quarters of the average expected lifespan in its country of origin, more preferably if it has surpassed the first four fifths of the average expected lifespan in its country of origin. An "elderly human" means a person with a chronological age of 65 years or older.

As set forth above, the present inventors surprisingly and unexpectedly found a synergy of cinnamaldehyde and zinc on the pharmacological activity of TRPA1. Using this synergy, the effective amount of cinnamaldehyde can be decreased by supplementing the cinnamaldehyde with small amount of zinc. Consequently, unlike cinnamaldehyde in the absence of zinc, the combination of cinnamaldehyde and zinc can promote a swallowing reflex at concentrations in food that are tolerable both in flavor/taste and in the gastrointestinal tract. Moreover, the synergy only requires a low concentration of zinc (in vitro <1 µM). Promotion of the swallowing reflex can include, for example, provoking a swallowing reflex, increasing the ability of the individual to swallow, increasing the efficacy of the swallow, decreasing a delay in swallowing, and combinations thereof.

Accordingly, the composition provided by the present disclosure comprises an amount of the cinnamaldehyde that is orally tolerable, for example does not cause an unpleasant mouth feeling, and, in combination with the zinc, effective to promote a swallowing reflex.

Cinnamaldehyde is available commercially. The cinnamaldehyde in the composition can be provided in a cinnamon essential oil extract, for example an extract from steam distillation of the oil of cinnamon bark; can be isolated cinnamaldehyde, for example isolated from cinnamon essential oil; or can be synthesized cinnamaldehyde, for example the product of aldol condensation of benzaldehyde and acetaldehyde. The concentration of cinnamaldehyde in the composition is preferably at flavouring concentration from 31.87 ppm (condiments, relishes) up to 6191 ppm (chewing gum) (Fenaroli's Handbook; Burdock, 2010). In an embodiment, the cinnamaldehyde is present in composition in an amount of about 100.0 ppm or less; 100 pm is equivalent to about 756 µM, the flavoring range in gelatins according to Fenaroli's Handbook (Burdock, 2010).

As non limiting examples, the cinnamaldehyde can be present in the following compositions as follows:
alcoholic beverage: up to 498.8 ppm, such as about 435.6 ppm
baked good: up to 367.4 ppm, such as about 273.8 ppm
chewing gum: up to 6191.0 ppm, such as about 1533.0 ppm
condiment or relish: up to 31.87 ppm, such as about 17.48 ppm
frozen dairy product: up to 77.96 ppm, such as about 72.98 ppm
fruit ice: up to 900.0 ppm, such as 900.0 ppm
gelatin or pudding: up to 109.4 ppm, such as about 100.3 ppm
gravy: up to 800.0 ppm, such as about 640.0 ppm
hard candy: up to 1003.0 ppm, such as about 792.2 ppm
meat product: up to 39.09 ppm, such as about 6.97 ppm
non-alcoholic beverage: up to 67.82 ppm, such as about 52.71 ppm
soft candy: up to 370.0 ppm, such as 370.0 ppm Preferred forms of zinc include zinc chloride, zinc sulfate, zinc lactate and zinc citrate. The cinnamaldehyde:zinc ratio is preferably 1:0.5 to 1:0.005, more preferably 1:0.03 (in molarity).

In an embodiment, the present disclosure provides a method comprising administering to an animal a composition comprising an amount of cinnamaldehyde and zinc that promotes a swallow reflex and is orally tolerable. Such a method is preferably employed in the treatment of oral pharyngeal dysphagia in the animal. The oral pharyngeal dysphagia may be a consequence of at least one of cancer, cancer chemotherapy, cancer radiotherapy, surgery for oral cancer, surgery for throat cancer, a stroke, a brain injury, a neurodegenerative disease, an elderly age of the patient, or a progressive neuromuscular disease, such as Parkinson's disease.

In an embodiment, the method prevents or treats aspiration pneumonia from dysphagia. Aspiration is entry of food or drink into the trachea (windpipe) and lungs and can occur during swallowing and/or after swallowing (post-deglutitive aspiration). Post-deglutitive aspiration generally occurs as a result of pharyngeal residue that remains in the pharynx after swallowing.

In a preferred embodiment, the cinnamaldehyde and zinc are administered in a nutritional supplement, such as a nutrient-dense beverage. In another preferred embodiment, the cinnamaldehyde and zinc are administered in a hydration supplement, preferably containing more than 83% free water and more preferably more than 90% free water. Such a supplement may be in the form of a thickened liquid. In yet another preferred embodiment, the cinnamaldehyde and zinc are administered in a texture-modified food.

The composition comprising cinnamaldehyde and zinc may be a medicament, a food product, a medical food, an oral nutritional supplement, a nutritional composition, an oral cosmetics or a supplement to a food product and is preferably orally administered. A medical food product is specially formulated and intended for the dietary management of diseases or medical conditions (e.g., prevent or treat diseases or undesirable medical conditions). A medical food product can provide clinical nutrition, for example fulfilling special nutritional needs of patients with a medical condition or other persons with specific nutritional needs. A medical food product can be in the form of a complete meal, part of a meal, as a food additive, or a powder for dissolution.

A food product, medical food or nutritional composition includes any number of optional additional ingredients, including conventional food additives, for example one or more proteins, carbohydrates, fats, acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers and/or vitamins. The optional ingredients can be added in any suitable amount.

A food product, medical food or nutritional composition can be in any oral nutritional form, e.g. as a health drink, as a ready-made drink, optionally as a soft drink, including juices, milk-shake, yogurt drink, smoothie or soy-based drink, in a bar, or dispersed in foods of any sort, such as baked products, cereal bars, dairy bars, snack-foods, soups, breakfast cereals, muesli, candies, tabs, cookies, biscuits, crackers (such as a rice crackers), and dairy products.

A supplement may be in the form of tablets, capsules, pastilles or a liquid, for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins or the like), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like.

The supplement can be added in a product acceptable to the consumer as an ingestible carrier or support. Non-limiting examples of such carriers or supports are a pharmaceutical, a food composition, and a pet food composition. Non-limiting examples for food and pet food compositions are milks, yogurts, curds, cheeses, fermented milks, milk-based fermented products, fermented cereal based products, milk-based powders, human milks, preterm formulas, infant formulas, oral supplements, and tube feedings.

EXAMPLES

The following non-limiting examples present in vitro scientific data developing and supporting the concept of administering the combination of cinnamaldehyde and zinc to synergistically activate TRPA1 to promote a swallowing reflex without imparting an intolerable taste or gastrointestinal effect.

Example 1

The in vitro activity of hTRPA1 expressed in CHO cells was measured for 10 μM cinnamaldehyde and 0.3 μM zinc individually, as well as the combination. The results are shown in FIG. 2 and show a synergistic effect when cinnamaldehyde and zinc are combined (Cin+Zinc). C+ represents the experimental positive control for this test and is cinnamaldehyde at 50 mM which give a maximum efficacy according to a dose-response curve.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for treating dysphagia, the method comprising administering to a patient having dysphagia a composition comprising an amount of a combination of cinnamaldehyde and zinc that provokes a swallow reflex in the patient, wherein the composition is a food product having a cinnamaldehyde:zinc ratio of 1:0.5 to 1.0.03 in molarity, and the cinnamaldehyde is present in the food product at a concentration of about 100 pm or less.

2. The method of claim 1 wherein the dysphagia is oral pharyngeal dysphagia associated with a condition selected from the group consisting of cancer, cancer chemotherapy, cancer radiotherapy, surgery for oral cancer, surgery for throat cancer, a stroke, a brain injury, a progressive neuromuscular disease, a neurodegenerative disease, an elderly age of the patient, and combinations thereof.

3. A method of reduction of risk and/or severity of aspiration pneumonia from dysphagia, the method comprising administering to a patient at risk thereof a composition comprising an amount of a combination of cinnamaldehyde and zinc that provokes a swallow reflex in the patient, wherein the composition is a food product having a cinnamaldehyde:zinc ratio of 1:0.5 to 1.0.03 in molarity, and the cinnamaldehyde is present in the food product at a concentration of about 100 pm or less.

4. The method of claim 3 wherein the cinnamaldehyde is present in the composition in an amount that is tolerable to ingest and, in combination with the zinc, effective to promote a swallowing reflex in the patient.

5. The method of claim 1 wherein at least a portion of the zinc is selected from the group consisting of zinc chloride, zinc sulfate, zinc lactate, zinc citrate and combinations thereof.

6. The method of claim 1 wherein the composition comprises cinnamon essential oil extract that provides at least a portion of the cinnamaldehyde.

7. The method of claim 1 wherein at least a portion of the cinnamaldehyde is selected from the group consisting of isolated cinnamaldehyde and synthesized cinnamaldehyde.

8. The method of claim 1 wherein the composition is a food product comprising a component selected from the group consisting of protein, carbohydrate, fat and combinations thereof.

* * * * *